United States Patent
Detmer

(10) Patent No.: US 6,443,896 B1
(45) Date of Patent: Sep. 3, 2002

(54) METHOD FOR CREATING MULTIPLANAR ULTRASONIC IMAGES OF A THREE DIMENSIONAL OBJECT

(75) Inventor: Paul Ross Detmer, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 65 days.

(21) Appl. No.: 09/641,306

(22) Filed: Aug. 17, 2000

(51) Int. Cl.⁷ .................................................. A61B 8/00

(52) U.S. Cl. ...................... 600/445; 600/443; 128/916; 73/618

(58) Field of Search .................................. 600/440, 447, 600/443, 441, 458; 128/916; 348/163; 73/602

(56) References Cited

U.S. PATENT DOCUMENTS

| | | | | |
|---|---|---|---|---|
| 4,581,636 A | * | 4/1986 | Blaker et al. | 348/163 |
| 5,546,807 A | * | 8/1996 | Oxaal et al. | 73/602 |
| 5,928,151 A | * | 7/1999 | Hossack et al. | 128/916 |
| 6,099,474 A | * | 8/2000 | Solek | 600/440 |
| 6,241,675 B1 | * | 6/2001 | Smith et al. | 128/916 |
| 6,276,211 B1 | | 8/2001 | Smith | |

OTHER PUBLICATIONS

Snyder et al., "Real–Time Orthogonal Mode Scanning of the Heart. I. System Design," JACC, vol. 7, No. 6, Jun. 1986, pp. 1279–1285.

* cited by examiner

Primary Examiner—Marvin M. Lateef
Assistant Examiner—Ruby Jain
(74) Attorney, Agent, or Firm—W. Brinton York, Jr.

(57) ABSTRACT

A method for creating multiple planar images of a volumetric region of an object without acquiring data from the entire volumetric region. The method includes sweeping a transducer across the volumetric region. At sampling positions during the sweep, ultrasonic beams from the transducer are transmitted into the volumetric region, which intersect one or more of a plurality of surfaces to be scanned. The number of transmitted beams during the sweep is fewer than the number of beams that would be transmitted to scan the entire volumetric region. Echoes from the volumetric region are received at the transducer in response to the transmitted beams. From the received echoes, planar images corresponding to the plurality of surfaces are formed. In a variation, the method includes receiving at the transducer fewer echoes from the volumetric region than the echoes that would be received from scanning the entire volumetric region. This enables the creation of planar images corresponding to buried surfaces within the volumetric region. Because only a finite plurality of surfaces of the region is being scanned rather than the entire volumetric region, planar images of high image quality and a broad field of view can be created and displayed in real-time.

22 Claims, 6 Drawing Sheets

DIRECTION OF MECHANICAL MOTION

METHOD FOR CREATING MULTIPLANAR ULTRASONIC IMAGES OF A THREE DIMENSIONAL OBJECT

TECHNICAL FIELD

This invention relates generally to ultrasonic imaging and, more particularly, to creating multiple planar ultrasonic images of an object in real-time, as the ultrasonic data is acquired.

BACKGROUND

A major advantage of three-dimensional ultrasonic imaging is the ability it provides to obtain unique image planes through the volume of an object such as a human body, image planes not available through conventional two-dimensional scanning. For example, through three-dimensional imaging techniques one can look simultaneously at several different cut planes of a region of tissue to thereby observe features from different angles. Alternatively, it may be desirable in certain instances, to view an image plane at a constant depth below the object surface such as the skin; such an image plane cannot be obtained with normal two-dimensional scanning because of the orientation of the ultrasonic probe relative to the object.

Generally, three-dimensional imaging techniques work by acquiring an entire volume of data in the region of interest, and then "slicing through" the data at appropriate angles to view desired planar images. Often a number of planar images can be displayed simultaneously on a computer monitor.

Prior three-dimensional ultrasonic imaging methods, however, must acquire data from the entire volumetric region of interest in order to construct three-dimensional images. These methods can typically acquire three-dimensional data at a rate of no more than one to two volumes per second. Consequently, these methods are relatively slow and not suitable for generating useful planar images in real-time, which is necessary to capture rapid changes in the region of interest. To speed up the data acquisition rate sufficiently to generate real-time planar images, the image quality or the field of view is sacrificed. This usually reduces the clinical usefulness of such images, especially in the areas of surgery, cardiology and obstetrics.

SUMMARY

In accordance with the invention, method and apparatus are disclosed for creating multiple planar images of a volumetric region of an object without acquiring data from the entire volumetric region. In one aspect of the invention, the method includes sweeping a transducer across the volumetric region. At sampling positions during the sweep, ultrasonic beams from the transducer are transmitted into the volumetric region and intersect one or more of a plurality of surfaces to be scanned, which surfaces can be planar or non-planar. The number of transmitted beams is fewer than the number of beams that would be transmitted to scan the entire volumetric region. Echoes from the volumetric region are received at the transducer in response to the transmitted beams. From the received echoes, planar images are formed corresponding to the plurality of surfaces scanned. Because only a finite plurality of surfaces of the region are being scanned rather than the entire volumetric region, planar images of high image quality and a broad field of view can be created and displayed in real-time.

In another aspect of the invention, the method includes processing fewer echoes from the volumetric region than the echoes that would be processed to image the entire volumetric region. This variation enables the creation of planar images corresponding to buried surfaces within the volumetric region.

DETAILED DESCRIPTION

Figure 1:
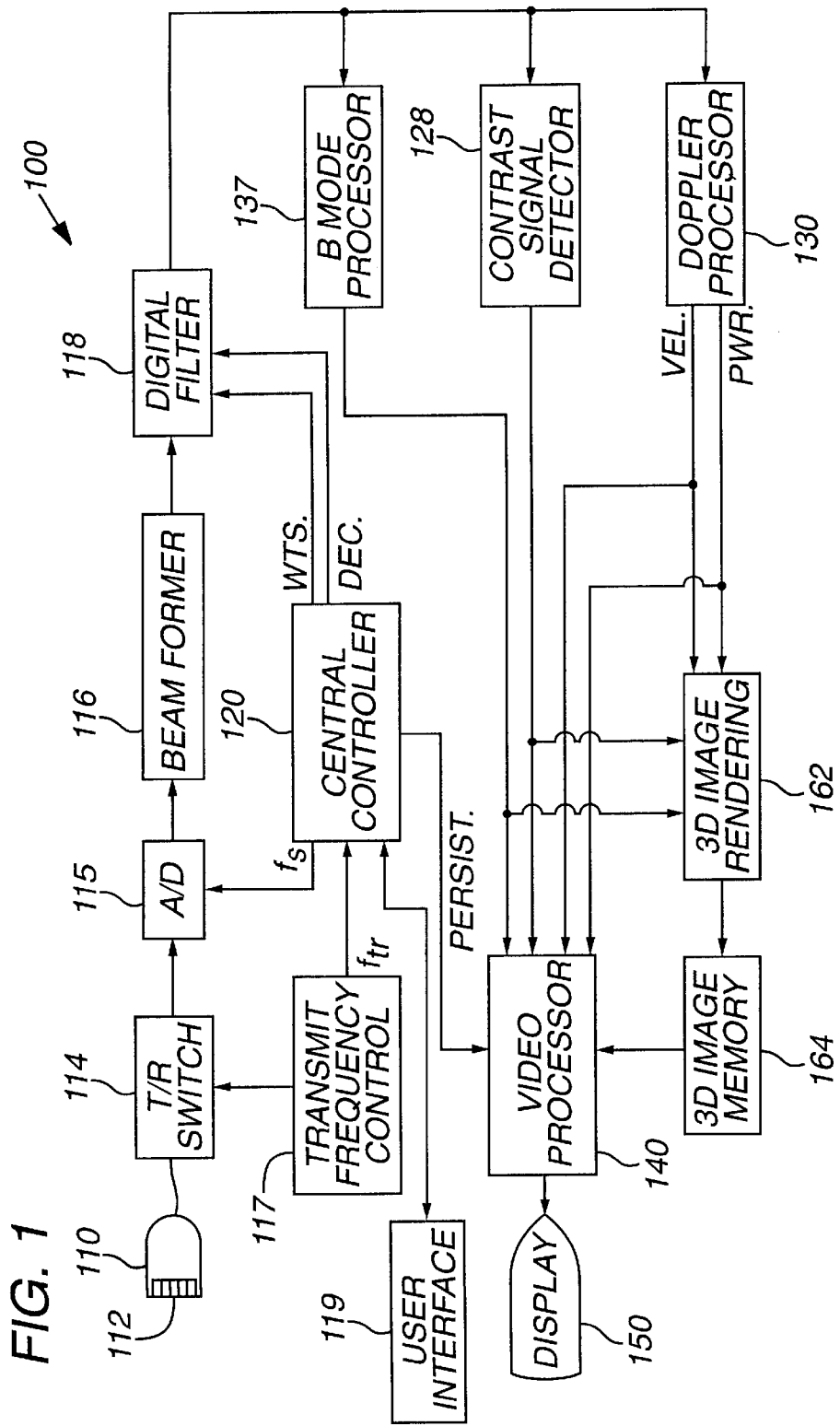
FIG. 1 is a block diagram of an ultrasonic diagnostic imaging system according to the invention.

FIG. 1 is a block diagram of an ultrasonic diagnostic imaging system 100 with which methods and apparatus in accordance with the invention can be used. It should be understood that the invention is not limited to use with this imaging system but is shown implemented therein only as an example. In the imaging system 100, a central controller 120 commands a transmit frequency control 117 to transmit a desired transmit frequency band. The parameters of the transmit frequency band, $f_{tr}$, are coupled to the transmit frequency control 117, which causes a transducer 112 of an ultrasonic probe 110 to transmit ultrasonic waves in the fundamental frequency band. It will be understood, of course, that any ultrasonic frequency or group of frequencies, known as a frequency signature, may be used, with due consideration of the desired depth of penetration and the sensitivity of the transducer and ultrasonic system.

The transducer 112 of the probe 110 comprises an array of discrete elements that transmit ultrasonic energy in the form of a beam, and receive echo signals returned in response to this transmission. The beam can be steered to scan different parts of an object by mechanically moving the probe or electronically adjusting the timing of the transmission for the various array elements. In image system 100, this steering is controlled by central controller 120. The controller 120, in turn, responds to commands from a user entered via a user system interface 119 that includes an interface program and a pointing device (such as a mouse, trackball, stylus, tablet, touch screen or other pointing device), keyboard, or other input device for conveying instructions to the central controller. Alternatively, the controller may be programmed to steer the beam automatically in a predetermined, default manner. The received signals are coupled through a transmit/receive (T/R) switch 114 and digitized by an analog-to-digital converter 115. The sampling frequency $f_s$, of the A/D converter is controlled by the central controller 120. The desired sampling rate dictated by sampling theory is at least twice the highest frequency $f_c$ of the received echoes. Sampling rates higher than the minimum requirement can also be used. The signal samples are delayed and summed by a beam former 116 to form coherent echo signals. The coherent echo signals are then filtered by a digital filter 118 to a desired passband. The digital filter 118 can also shift the frequency band to a lower or baseband frequency range. The characteristics of the digital filter are controlled by the central controller 120, which provides the filter with multiplier weights and decimation control. Preferably the arrangement is controlled to operate as a finite impulse response (FIR) filter, and performs both filtering and decimation. A wide range of filter characteristics is possible through programming of the weighting and decimation rates of the filter, under control of the central controller 120. The use of a digital filter allows the advantage of flexibility in providing different filter characteristics. A digital filter can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence, simply by changing the filter coefficients during signal processing.

From the digital filter 118, the filtered echo signals are detected and processed by a B mode processor 137, a contrast signal detector 128, or a Doppler processor 130. The B mode processor performs functions that include, but are not limited to, frequency compounding, spatial compounding, harmonic image formation, and other typical B mode functions that are well known in the art. The Doppler processor applies conventional Doppler processing to the echo signals to produce velocity and power Doppler signals. The outputs of the processors 137 and 130 and contrast signal detector 128 are coupled to a video processor 140 for display as a two-dimensional ultrasonic image on the display 150. The central controller 120 keeps track of the sequence of the incoming signals, and so enables the video processor 140 to place the current data in the forming image. As signals are received by the video processor 140, the data is fed to the display, producing rasterized images. The outputs of the two processors and contrast signal detector are also coupled to a three-dimensional image rendering processor 162 for the rendering of three-dimensional images, which are stored in an image memory 164 and provided from there to the video processor 140. Three-dimensional rendering may be performed in a conventional manner. With this arrangement, an operator can select among the outputs of the contrast signal detector 128 and the processors 137 and 130 for two- or three-dimensional display of an ultrasonic image.

The system of FIG. 1, through the operation and control of the probe 110, transducer 112, the video processor 140, and/or the image rendering processor 162, provides the ability to create multiple real-time planar images of a volumetric region of an object such as a human body, while the body is being scanned. These planar images, when taken as slices through a body, have known geometric relationships to each other, enabling a diagnostician to view body features from different orientations. The clinician may wish to adjust the relative angles of the slices to visualize spatial relationships of tissue features. Through user interface 119, an operator can adjust the orientation of the slices displayed to align them with the features of interest in the image. Real-time performance is achieved by generating only certain ultrasonic beams needed to construct the desired planar images, rather than the much greater number of beams that would have to be transmitted to scan the entire volumetric region.

Figure 2A:
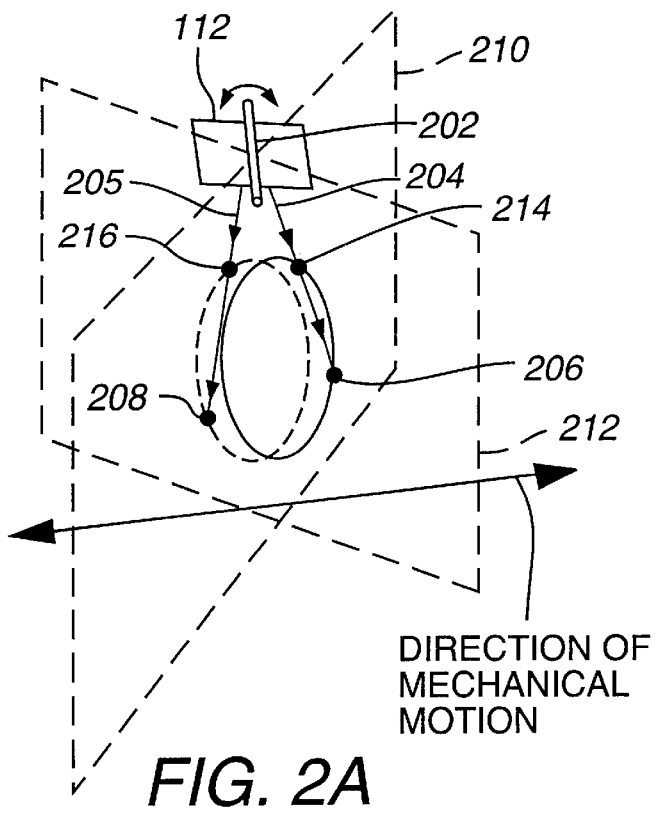
FIGS. 2A and B show a method for creating a set of planar images according to the invention, using a first embodiment of a transducer.
Figure 2B:
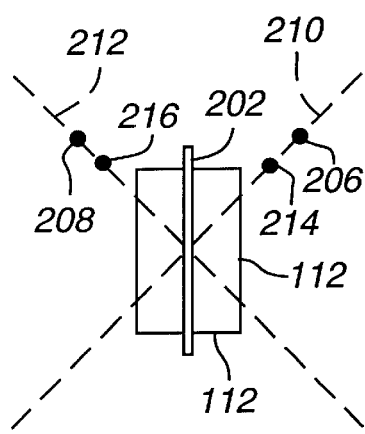

FIGS. 2A and 2B show one method for creating a set of planar images according to the invention, using the probe 110 and its transducer 112 to obtain a first set of surfaces (typically planar, or non-planar, including saddle-shaped, i.e., having the same or different curvatures in different directions of travel along the surface), such as orthogonal planes 210 and 212. The transducer 112 is mounted on a gimbal 202 or other pivotable support and is powered to sweep, or scan, back and forth across the region of interest of a body, as indicated in the figure. The sweep frequency is preferably at least eight sweeps per second to allow planar images to be created in real-time, though higher or lower rates can be used depending upon the degree of real-time imaging desired. As the transducer 112 sweeps across the region of interest, it generates beams at successive sampling positions, such as the position shown in the figure. At each sampling position, the transducer 112 generates a first beam comprising signals from the individual transducer elements that converge on a focal point in a plane 210. At the position shown in the figure, one such beam 204 converges on point 206 in plane 210. At each sampling position in this example, the transducer 112 also generates a second beam comprising signals from the individual transducer elements, that converge on a focal point in a plane 212. At the position shown in the figures, a beam 205 converges on point 208 in plane 212. At each sampling position of the transducer, then, two beams are emitted, one along each respective line in each of the two respective planes. Through selective steering, gating, and/or focusing of the echo signals, which are techniques well-known in the art for enabling selective receiving of information from chosen points, only echo signals that travel in the planes of interest are received and processed in response to the transmitted beams. In plane 210, for example, reflections at points 214 and 206 on beam 204 represent boundaries between different entities within the region of interest, such as a cavity and tissue. Similarly, in plane 212, reflections at points 216 and 208 on ray 205 also represent boundaries between different entities within the region of interest.

The above scanning method for generating two planar images is preferred because of its speed, but is not exclusive. Variations are possible. If desired, additional beams can be generated which lie in and thereby define additional planes, or intersect additional surfaces. Each additional beam, or course, takes additional time to generate and therefore affects the sweep rate. The desired number of planes and their orientation is conveyed to central controller 120 through user interface 119. In addition, the transducer 112 can be controlled to emit beams directed toward more than one point in each plane. Alternatively, the transducer can be controlled to emit beams at fewer than all surfaces at each sampling position, as long as the beams lie in at least two planes, or intersect at least two non-planar surfaces, or lie in at least one plane and intersect at least one non-planar surface, per sweep. These and other obvious variations can produce multiple planar images in real-time, but at different rates and with different resolutions, depending on the variation chosen. Furthermore, any two-dimensional ultrasonic imaging technique, for example, B mode, contrast signal detection, harmonic imaging, or Doppler imaging, can be applied equally well with this data acquisition scheme.

The data acquired from the two planes 210 and 212 are used by one or more of the processors 137, 130, or the contrast signal detector 128 to construct the corresponding planar images. The planar images are preferably created at the sweep rate to provide real-time imaging. The planar images can be simultaneously displayed side-by-side by the video processor 140, or in a three dimensional perspective view on the display 150 as the volumetric region is continuously scanned, or viewed later.

Figure 3A:
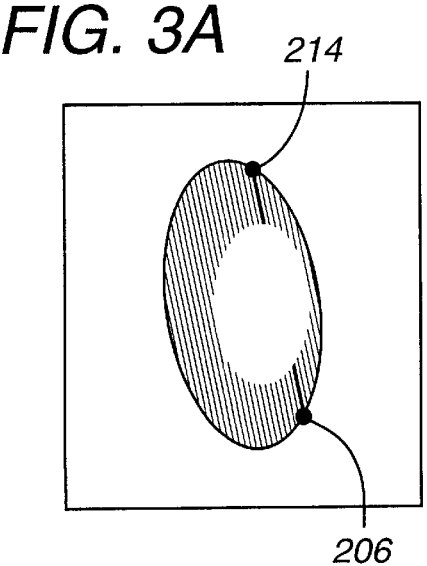
FIGS. 3A and B show a display, in real time, of the planar images created by the method of FIG. 2.
Figure 3B:
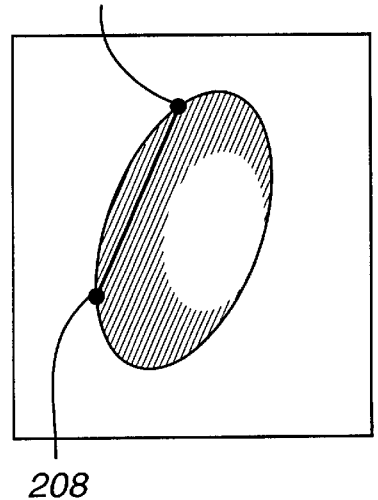

The obtained planar images each represent a cross-section of the body under study. The transducer 112 sweeps through a total angle that subtends the region of interest. To obtain real-time images, the sweeping motion is repeated back and forth over the region of interest, producing a succession of planar images over time. FIGS. 3A and B show examples of such planar images, constructed from data acquired from planes 210 and 212. The limited data thus collected enables these planar images to be constructed and refreshed in real-time, for instance, eight times per second or more frequently. These images can be used to determine, for instance, changes in cavity volume over time. The images can be saved and later played back at a rate determined by the user, on a frame-by-frame basis, enabling a diagnostician to carefully study the motion to determine for instance, the maximum and minimum dimensions of a variablesized cavity such as the heart left-ventricle. As noted above, the present method can be used to acquire data from additional planes and/or non-planar surfaces, should it be deemed advantageous to do so. If, for instance, an organ was suspected to have an off-axis tumor that might not by intersected by planes 210 or 212, other planes of different orientations, or else parallel to one of the planes and displaced in the direction perpendicular to that plane, might be chosen to augment or replace images shown for planes 210 and 212.

Figure 4A:
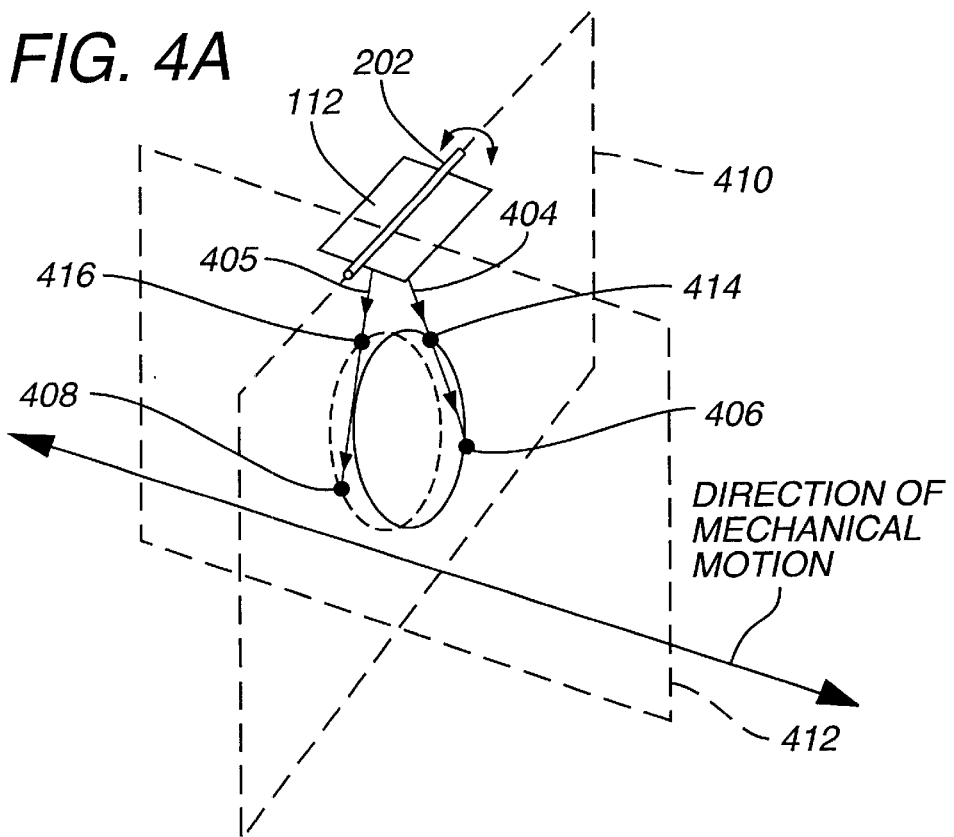
FIGS. 4A and B show a variation on the method of FIGS. 2A and B.
Figure 4B:
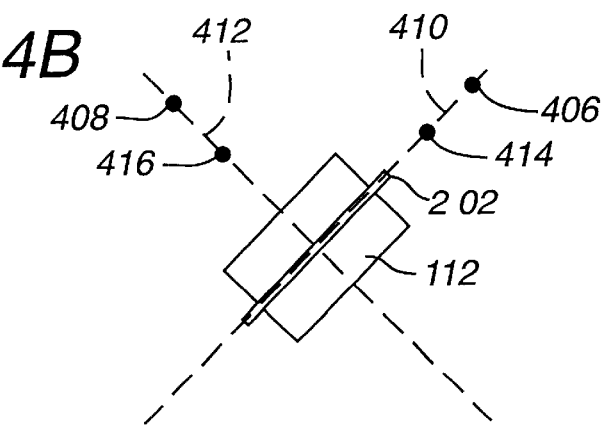

FIGS. 4A and 4B show the above method in use to acquire data from a set of planes with an orientation different from the planes in FIGS. 2A and 2B. In this embodiment, a plane 410 is parallel to the axis of rotation of gimbal 202 and transducer 112, and a plane 412 is orthogonal to both that axis of rotation and plane 410. As the transducer 112 sweeps through the sampling positions, only one beam is generated at most transducer sampling positions lying on plane 412, such as represented by ray 405 whose signals are shown reflecting, for instance, from points 416 and 408. It is only when the transducer is at the center-point in its sweep that multiple beams are generated at a transducer sampling position, which beams lie in and thereby define the aligned plane 410. Ray 404 represents one of these beams, showing signals reflected from points 414 and 406. Because of the time required to generate multiple beams and acquire multiple lines of data, the method may require that the sweep of the transducer 112 be slowed or stopped at this center-point, to ensure that the data is acquired successfully.

Figure 5A:
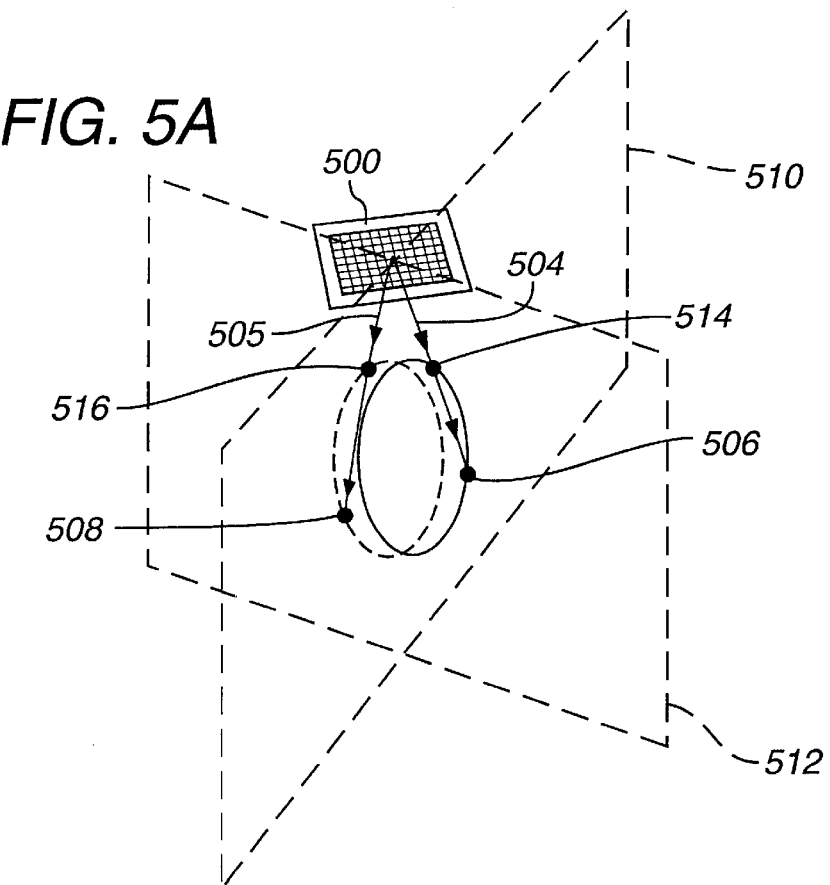
FIGS. 5A and B show a second embodiment of a transducer for use with the invention.
Figure 5B:
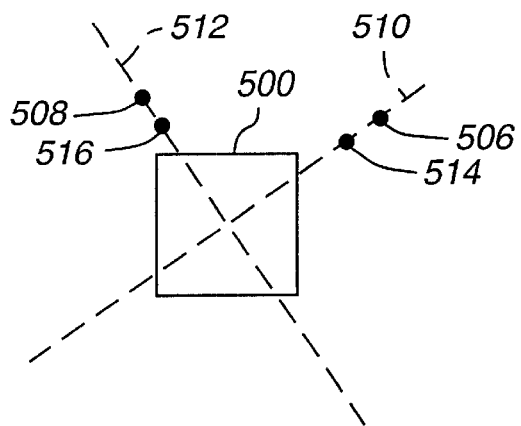

FIGS. 5A and 5B show a second embodiment of a transducer 500 that can be used to obtain data from a set of planes 510 and 512. This embodiment generates beams such as beam 504 that lies in plane 510, intersecting points 514 and 506; also beam 505 that lies on plane 512, intersecting points 516 and 508. The rays emanating from two-dimensional array transducer 500 can be electronically steered in two dimensions, thus avoiding the need to mechanically sweep the transducer across the volumetric region of interest. In similar fashion, data is received from the lines of interest in the respective planes using well-known beam steering and focusing and/or gating techniques applicable to a two-dimensional array transducer.

Figure 6A:
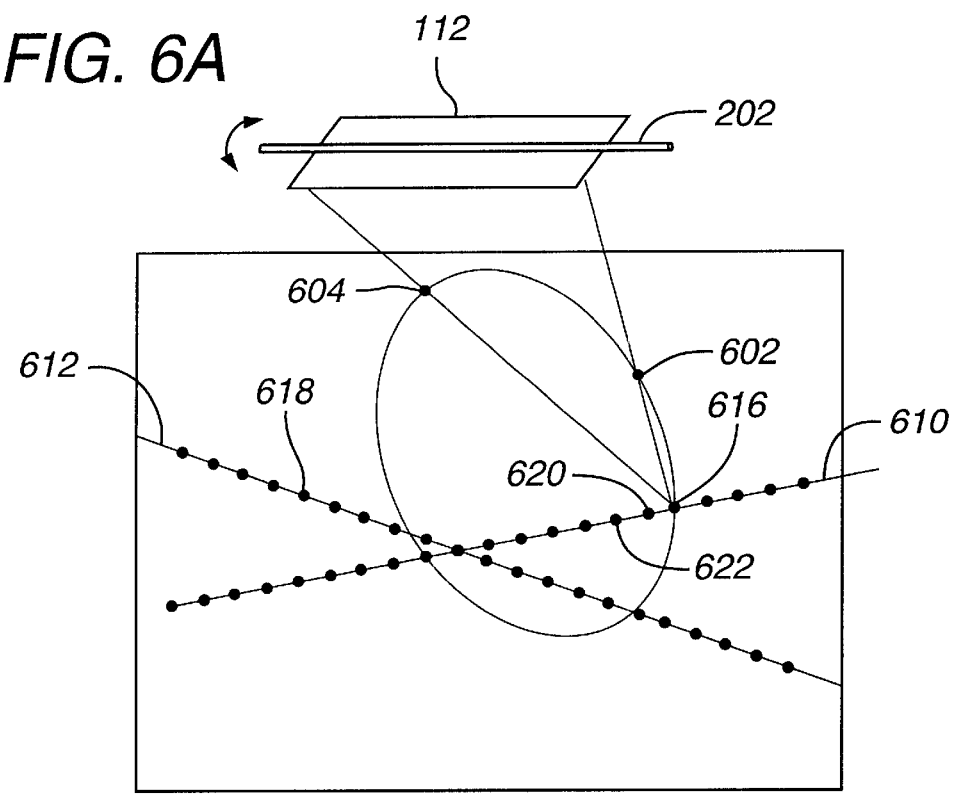
FIGS. 6A and B show another method for creating a set of planar images according to the invention.
Figure 6B:
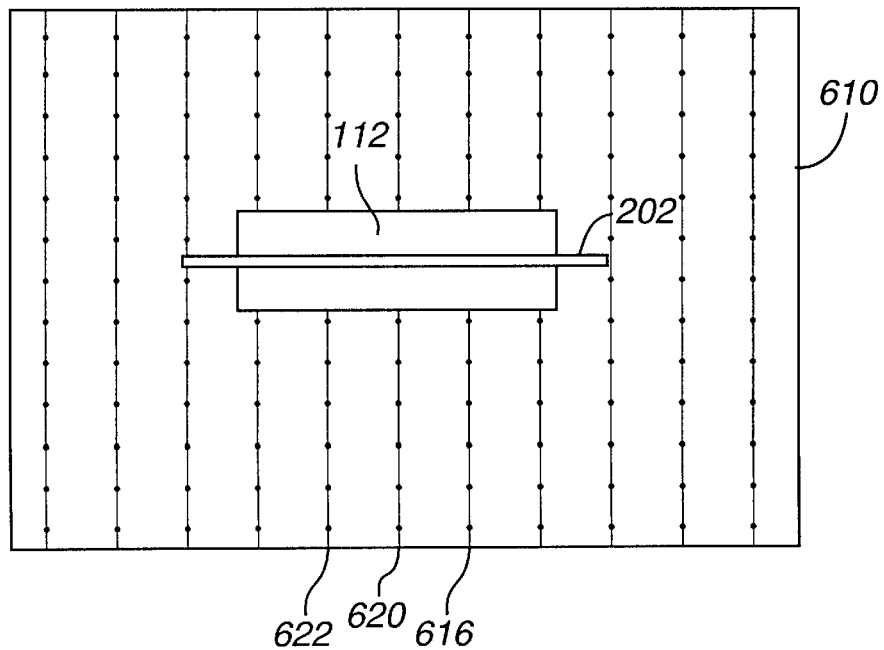

FIGS. 6A and 6B show a related method for acquiring data from one or more planes that are not orthogonal to the plane of the transducer 112, such as buried planes 610 and 612. FIG. 6A is a side view showing that, at a given position in the transducer's rotational travel, a number of beams is generated to gather data from points lying in a line that can be of constant depth (i.e., a line of constant depth here is one which is perpendicular to the plane of FIG. 6A) such as lines 616, 620 and 622 (represented by points 616, 620 and 622 respectively in the perspective shown) in the plane 610, or line 618 in plane 612. FIG. 6B is a top view showing parallel lines in plane 610, with each line such as lines 616, 620 and 622, at its respective constant depth. Moreover, through dynamic steering, gating, and focusing of received echoes, data can be obtained for points along the beam between the transducer 112 and any point on the plane of interest, such as points 602 and 604 in FIG. 6A. Alternately, scanning can be done by steering, gating, and focusing on points along lines of any orientation within a plane such as plane 610, which can be for instance, parallel lines, concentric circles, or in general any set of lines that covers the plane of interest or portion thereof.

As a further generalization to all cases considered heretofore, data can be acquired from two-dimensional surfaces (also called "surfaces"henceforth) that are planar or non-planar. The same procedure applies.

Figure 7A:
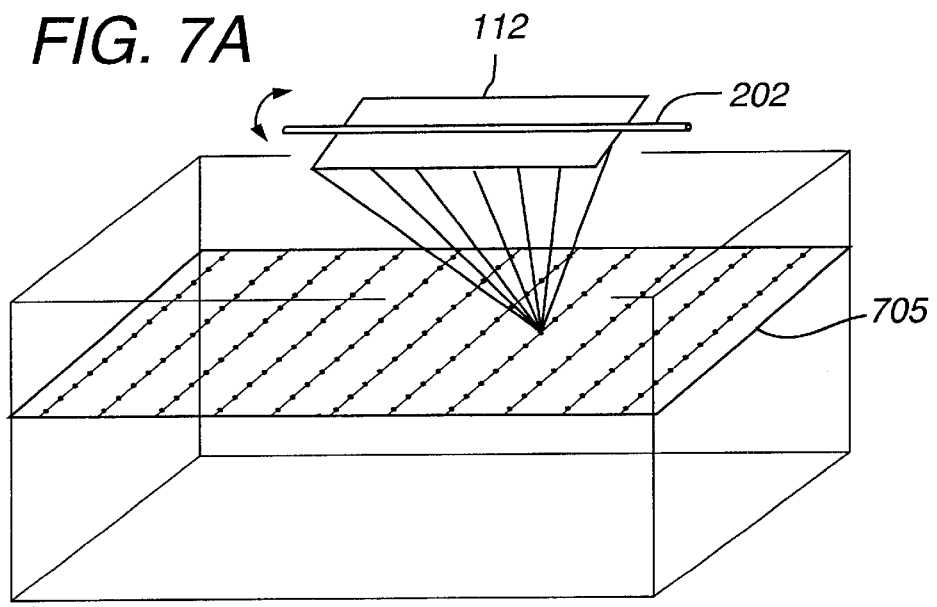
FIGS. 7A and B show a variation on the method of FIGS. 6A and B.
Figure 7B:
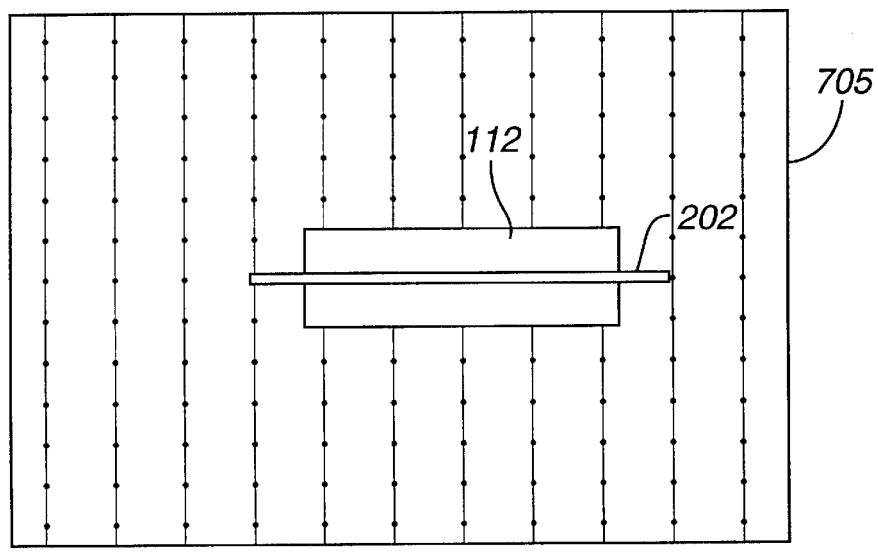

A special case of acquiring data from buried surfaces is shown in FIGS. 7A and 7B, wherein a single horizontal plane 705, at a constant depth less than the greatest depth of the body, is scanned. The data so obtained can be used to display an image of plane 705, as well as data from a collection of points lying anywhere between the plane and the transducer. Data from the latter points are collected through dynamic focusing of the echoes received from each of the beams directed toward plane 705. The amount of data collected in this fashion is less than the totality of data that would be collected in the case of three-dimensional imaging of the entire region of interest. In similar fashion to the examples discussed above, a single non-planar surface could be scanned.

Having illustrated and described the principles of the invention in exemplary embodiments, it should be apparent to those skilled in the art that the illustrative embodiments can be modified in arrangement and detail without departing from such principles. In view of the many possible embodiments to which the principles of the invention can be applied, it should be understood that the illustrative embodiments are intended to teach these principles and are not intended to be a limitation on the scope of the invention. I therefore claim as my invention all that comes within the scope and spirit of the following claims and their equivalents.

I claim:

1. A method for creating multiplanar ultrasonic images of a volumetric region of an object, comprising:

mechanically sweeping a transducer across the volumetric region;

at sampling positions during the sweep, transmitting ultrasonic beams from the transducer into the volumetric region which intersect one or more of a plurality of surfaces to be scanned, the beams intersecting at least two surfaces per sweep, the number of transmitted beams during the sweep being fewer than the number of beams that would be transmitted to scan the entire volumetric region;

receiving at the transducer echoes from the volumetric region in response to the transmitted beams; and from the received echoes, forming planar images corresponding to the plurality of surfaces.

2. The method of claim 1 wherein the plurality of surfaces is two.

3. The method of claim 1 wherein at least two of the surfaces are planes, and beams transmitted at each sampling position lie respectively in each of the respective planes to be scanned.

4. The method of claim 3 wherein the number of planes is at least two.

5. The method of claim 4, wherein two of the planes are orthogonal to each other.

6. The method of claim 3 wherein at least one of the surfaces is planar, and a plurality of the transmitted beams defines each planar surface.

7. The method of claim 3 wherein for the planar surfaces, the transmitted beams lie respectively in only the respective planes to be scanned.

8. The method of claim 1 wherein the surfaces intersect within the volumetric region.

9. The method of claim 1 wherein forming planar images from the received echoes includes processing echo signals with a B mode processor, contrast signal detector, or Doppler processor.

10. The method of claim 9 wherein the B mode processor performs functions including frequency compounding, spatial compounding, harmonic image formation, or combinations thereof.

11. The method of claim 1 including displaying the planar images after each sweep, and wherein the sweeping, transmitting, receiving, and forming are repeated at a sufficient rate to refresh the planar images at a real-time rate of display.

12. The method of claim 11 wherein the planar images are refreshed a rate of at least eight times per second.

13. The method of claim 1 wherein only echoes received by the transducers from points on the surfaces to be scanned are processed to form images.

14. An apparatus for creating multiplanar ultrasonic images of a volumetric region of an object, comprising:

an ultrasonic transducer adapted to mechanically sweep across the volumetric region;

a controller coupled to the transducer and adapted to cause the transducer to transmit, at a plurality of sampling positions during the sweep, ultrasonic beams into the volumetric region which intersect one or more of a plurality of surfaces to be scanned, the beams intersecting at least two surfaces per sweep, the number of transmitted beams during the sweep being fewer than the number of beams that would be transmitted to scan the entire volumetric region; and a processor coupled to the transducer and adapted to form planar images corresponding to the plurality of surfaces from data acquired by the transducer.

15. The apparatus of claim 14, wherein at least one of the surfaces to be scanned is planar, and the ultrasonic beams scanning the planes lie respectively in the respective planar surfaces to be scanned.

16. The apparatus of claim 14 wherein the controller is adapted to cause the transducer to transmit, at each sampling position, ultrasonic beams that intersect each of the surfaces.

17. The apparatus of claim 16 wherein at least one of the surfaces is planar, and the ultrasonic beams transmitted by the transducer lie respectively in the respective planar surfaces.

18. A method for imaging with an ultrasonic diagnostic imaging system having an array transducer located in a plane above a volumetric region to produce two or more two dimensional images of surfaces within the volumetric region comprising:

transmitting beams from the array transducer in cycles to sample points on at least two surfaces within the volumetric region which are located in planes which intersect the plane of the array transducer, the surfaces each having a depth dimension extending away from the array transducer and a lateral dimension extending substantially parallel to the plane of the array transducer, the number of transmitted beams in a cycle being sufficient to produce images of the surfaces and fewer than the number of beams that would be transmitted to scan the entire volumetric region;

receiving at the array transducer echoes from the surfaces in response to the transmitted beams; and processing the received echoes to produce planar images corresponding to the surfaces which have a finite lateral dimension at the deepest and shallowest depths of at least one of the planar images.

19. The method of claim 18, wherein processing further comprises processing the received echoes to produce two rectangular images.

20. The method of claim 18, wherein transmitting beams comprises transmitting beams to sample points on at least two surfaces within the volumetric region which are located in planes which are orthogonal to the plane of the array transducer.

21. The method of claim 18, wherein transmitting beams comprises transmitting beams to sample points on at least two surfaces within the volumetric region which are located in planes which intersect each other within the volumetric region.

22. The method of claim 18, wherein transmitting beams further comprises transmitting beams which lie within the planes within the volumetric region in which the surfaces are located.

* * * * *